United States Patent
Sugarman

(10) Patent No.: US 10,722,503 B2
(45) Date of Patent: Jul. 28, 2020

(54) GLITAZONES FOR TOPICAL APPLICATION

(71) Applicant: Jeffrey L. Sugarman, Santa Rosa, CA (US)

(72) Inventor: Jeffrey L. Sugarman, Santa Rosa, CA (US)

( * ) Notice: Subject to any disclaimer, the term of this patent is extended or adjusted under 35 U.S.C. 154(b) by 0 days.

(21) Appl. No.: 16/340,286

(22) PCT Filed: Feb. 21, 2018

(86) PCT No.: PCT/US2018/018907
§ 371 (c)(1),
(2) Date: Apr. 8, 2019

(87) PCT Pub. No.: WO2018/156552
PCT Pub. Date: Aug. 30, 2018

(65) Prior Publication Data
US 2019/0282556 A1   Sep. 19, 2019

Related U.S. Application Data

(60) Provisional application No. 62/461,878, filed on Feb. 22, 2017.

(51) Int. Cl.
| | | |
|---|---|---|
| *A61K 31/425* | (2006.01) | |
| *A61K 31/44* | (2006.01) | |
| *A61K 31/4439* | (2006.01) | |
| *A61P 17/00* | (2006.01) | |
| *A61K 9/00* | (2006.01) | |
| *A61K 45/06* | (2006.01) | |
| *A61K 9/06* | (2006.01) | |

(52) U.S. Cl.
CPC ........ *A61K 31/4439* (2013.01); *A61K 9/0014* (2013.01); *A61K 9/06* (2013.01); *A61K 45/06* (2013.01); *A61P 17/00* (2018.01)

(58) Field of Classification Search
CPC .................................................. A61K 31/4439
USPC ................................................. 514/369, 342
See application file for complete search history.

(56) References Cited

U.S. PATENT DOCUMENTS

2006/0159648 A1*  7/2006 Davis ................... A61K 9/0014
                                                    424/70.14
2012/0184584 A1*  7/2012 Roses ................ A61K 31/4439
                                                    514/342

FOREIGN PATENT DOCUMENTS

WO    2004/073622 A2    9/2004
WO    2015/179282 A1    11/2015

OTHER PUBLICATIONS

Dozsa et al. "PPAR-gamma-mediated and arachidonic acid-dependent signaling is involved in differentiation and lipid production of human sebocytes," J. Investigative Dermatology, 2014, vol. 134, pp. 910-920 (Year: 2014).*
Behshad et al., "A Retrospective Case Series Review of the Peroxisome Proliferator-Activated Receptor Ligand Rosiglitazone in the Treatment of Atopic Dermatitis," Arch Dermatol (2008) 144(1):84-88.
Gruber et al., "Sebaceous Gland, Hair Shaft, and Epidermal Barrier Abnormalities in Keratosis Pilaris with and without Filaggrin Deficiency," The American Journal of Pathology (2015) 185(4):1012-1021.
Bhagavathula et al., "BP-1107 [{2-[4-(2,4-Dioxo-thiazolidin-5-ylmethyl)-phenocy]-ethyl}-methyl-amide]: A Novel Synthetic Thiazolidinedione That Inhibits Epidermal Hyperplasia in Psoriatic Skin-Severe-Combined Immunodeficient Mouse Transplants after Topical Application," The Journal of Pharmacology and Experimental Therapeutics (2005) 315(3):996-1004.
Konger et al., "Mice deficient in epidermal PPARγ exhibit loss of sebaceous glands as well as augmented apoptosis and inflammation in response to ultraviolet B," The Fased Journal (2010) 24(1).
Marcelo et al., "Fatty Acids, thiazolidinediones, and VP16-PPARγ activate PPARγ in human keratinocytes and inhibit keratinocyte cell growth in vitro," (2004) 122(3).
Ma et al., "Lack of efficacy of tropical cyclosporin A in atopic dermatitis and allergic contact dermatitis," Acta Derm Venereol. (1991) 71(5):452-454.
Mirmirani et al., "Lichen Planopilaris Treated with a Peroxisome Proliferator Activated Receptor γ Agonist," Arch Dermatol. (2009) 145(12):1363-1366.
Reisz et al., "Licehn Sclerosus and data science: using an age, site and gender specific disease to define correlation and causality," Res. J. of Women's Health (2015) 2:1.
Sertznig et al., "Peroxisome Proliferator-Activated Receptors (PPARs) and the Human Skin," American Journal of Clinical Dermatology (2008) 9(1):15-31.
Trivedi et al., "Peroxisome Proliferator-Activated Receptors Increase Human Sebum Production," Journal of Investigative Dermatology (2006) 126:2002-2009.
Gerbig, "Treating keratosis pilaris," J. Am. Acad. Dermatol. Letters, 47(3): 457 (2002).
Zouboulis, "Isotretinoin Revisited: Pluripotent Effects on Human Sebaceous Gland Cells," J. of Investigative Dermatology 126: 2154-2156 (2006).
Thomas et al., "Keratosis Pilaris Revisited: Is It More Than Just a Follicular Keratosis?" In. J. Trichology, 4(4): 255-258 (2012).
Patel et al., "Unique Cutaneous Reaction to Second- and Third-Generation Tyrosine Kinase Inhibitors for Chronic Myeloid Leukemia," Dermatology 232: 122-125 (2016).
Wang et al., "Keratosis Pilaris and its Subtypes: Associations, New Molecular and Pharmacologic Etiologies, and Therapeutic Options," Am. J. of Clinical Derm. 19: 733-757 (2018).

* cited by examiner

*Primary Examiner* — Shengjun Wang
(74) *Attorney, Agent, or Firm* — Medler Ferro Woodhouse & Mills PLLC

(57) ABSTRACT

Glitazone compounds, such as pioglitazone, are useful for topical treatment of dermatologic conditions, such as keratosis pilaris, that are associated with a decrease in number or function of sebocytes.

9 Claims, No Drawings

GLITAZONES FOR TOPICAL APPLICATION

CROSS-REFERENCE TO RELATED APPLICATIONS

This application claims the benefit of the filing date of U.S. provisional application No. 62/461,878, filed on Feb. 22, 2017 as attorney docket no. 708.0001, the teachings of which are incorporated herein by reference in their entirety.

BACKGROUND

Field of the Invention

This invention pertains to the field of pharmaceutical formulations for topical application to the skin and particularly to the use of glitazones for topical therapy to the skin.

Description of the Related Art

This section introduces aspects that may help facilitate a better understanding of the invention. Accordingly, the statements of this section are to be read in this light and are not to be understood as admissions about what is prior art or what is not prior art.

Keratosis pilaris (KP), also known as follicular keratosis or lichen pilaris is a common, autosomal dominant, genetic follicular condition characterized by the appearance of rough, often red, bumps on the skin. It most often appears on the back, outer sides of the arm, face, thighs, and buttocks, although KP can also occur on the hands, and tops of legs, sides, or any body part except glabrous skin like the palms of hands or soles of feet. When the lesions appear on the face, KP may be mistaken for acne.

KP does not bear any known, long-term health implications, nor is it associated with increased mortality or morbidity although some disorders that cause morbidity have KP as one of their features. KP itself is harmless, although sometimes may be itchy and irritated. Those afflicted with KP are generally quite bothered by its appearance and by the feel that the bumps impart to the involved skin. KP sometimes disappears or improves by adulthood, and therefore medical treatment is not always necessary. Many individuals may, however, seek treatment for this condition for cosmetic reasons.

KP is believed to result from the buildup of keratin within the follicle. The keratin forms a keratotic plug that blocks the opening of the hair follicle. Usually many plugs form, causing patches of rough, bumpy skin. Often there is surrounding redness or inflammation. In addition, the number of sebaceous glands in the skin affected by KP is generally reduced.

There are no truly effective treatments for KP and the etiology is unknown. Treatments that are often utilized, with varying results, include the use of topical exfoliants such as those formulations containing alpha hydroxy acids such as lactic acid, or topical retinoids. Corticosteroids have been used to suppress the associated inflammation. Such treatments, when used regularly, may temporarily improve the appearance of skin. However, upon cessation of treatment, the condition returns and, even with medical treatment, KP may persist for years.

Glitazones, also known as thiazolidinediones, are a class of orally administered drugs that have been used in the management of diabetes mellitus. Members of the glitazone class of drugs that have been marketed include pioglitazone (ACTOS®, Takeda Pharmaceuticals U.S.A., Dearfield, Ill.); rosiglitazone (AVANDIA®, GlaxoSmithKline, Philadelphia, Pa.); lobeglitazone (DUVIE®, Chung Kun Dang, Seoul, Korea); and troglitazone, (REZULIN®, Pfizer, New York, N.Y.). Other members of the glitazone class of drugs include netoglitazone, rivoglitazone, and ciglitazone.

Glitazones act by activating PPARs (peroxisome proliferator-activated receptors), a group of nuclear receptors, with greatest specificity for $PPAR_\gamma$ (gamma). Trivedi, Journal of Investigative Dermatology, 126:2002-2009 (2006), discloses that activation of PPAR receptors by treatment with glitazone drugs causes an increase in sebum production in patients suffering from acne. This result is undesirable because acne is associated with, and is likely due in part to, increased sebum production.

Mirmirani et al, Arch. Dermatol., 145(12):1363-1366 (2009), reported that systemic pioglitazone was effective in the treatment of lichen planopilaris, a rare disorder that lead to permanent hair loss.

The vast majority of active pharmaceutical ingredients (APIs or drug substances) for systemic action are given orally. However, bioavailability varies widely among drug substances and drug classes. For example, some drug substances for systemic use cannot be administered orally because of inadequate or unreliable bioavailability from the gastrointestinal tract. Such APIs must be administered by the parenteral route. Transdermal administration via an occlusive patch provides a highly desirable sustained delivery of APIs. However, only a very few drugs can be delivered transdermally in sufficient quantity for a therapeutic effect. This is because one of the primary functions of the skin is to act as a protective barrier keeping chemicals from getting into the body, and the skin is a formidable barrier to APIs. In contrast, the intestinal wall is a semi-permeable membrane which facilitates the absorption of chemicals (vitamins, peptides, sugars, fats, etc.). It is well known by pharmaceutical scientists that oral bioavailability does not mean an API will have sufficient penetration into the skin to be effective in treating a skin disease when placed in a topical formulation.

For instance, Ma et al. ("Lack of efficacy of topical cyclosporin A in atopic dermatitis and allergic contact dermatitis", Acta Derm Venereol. 1991; 71(5):452-4.) attempted to alter the delivery route of oral cyclosporin A (CsA) which had demonstrated its effectiveness in the treatment of psoriasis and atopic dermatitis to avoid systemic adverse events. Efforts were made to develop a topical CsA formulation. Three topical CsA formulations were tested, but there was no significant improvement found in atopic dermatitis patients and allergic contact dermatitis patients.

Even with optimized formulations there are many drugs that have been tried topically and have failed because of inadequate delivery into the skin; however, these failures are seldom reported in the literature.

Reisz and Chakraborty ("Lichen sclerosus and data science: using an age, site and gender specific disease to define correlation and causality", Res. J. of Women's Health., 2:1, DOI: 10.7243/2054-9865-2-1 (2015)), reported the treatment of lichen sclerosus, a disease of unknown etiology that affects the vulvar region of menopausal women, with a topical formulation containing a mixture of pioglitazone 30 mg/oz in petrolatum.

SUMMARY OF THE INVENTION

In an embodiment of the invention, is a method for treating a dermatologic condition that is associated with a decrease in number or function of sebocytes, the method comprising topically applying to skin of an individual affected by the dermatologic condition a pharmaceutical formulation comprising a therapeutically effective amount of at least one glitazone compound.

In the foregoing embodiment, the pharmaceutical formulation may comprise a vehicle or carrier in which the at least one glitazone compound is dissolved, dispersed, suspended, or emulsified.

In each of the foregoing embodiments, the at least one glitazone compound can be selected from the group consisting of pioglitazone, rosiglitazone, lobeglitazone, troglitazone, netoglitazone, rivoglitazone, and ciglitazone, or the at least one glitazone compound is pioglitazone.

In each of the foregoing embodiments, the dermatologic condition can be keratosis pilaris.

In each of the foregoing embodiments, the pharmaceutical formulation can be in the form selected from the group consisting of creams, lotions, ointments, solutions, emulsions, gels, sprays, and foams.

In each of the foregoing embodiments, the method may further comprise applying to the skin at least one other active pharmaceutical ingredient selected from the group consisting of a corticosteroid, a retinoid, and an exfoliant such as an alpha-hydroxy acid or beta-hydroxy acid such as glycolic acid, lactic acid, malic acid, citric acid, alpha-hydroxyoctanoic acid, alpha-hydroxycaprylic acid, and hydroxycaprylic acid and salicylic acid, wherein the at least one other active pharmaceutical ingredient may be contained within the same pharmaceutical formulation as the at least one glitazone compound or may be applied in a separate pharmaceutical formulation.

In each of the foregoing embodiments, the pharmaceutical formulation may not contain any active pharmaceutical ingredient other than the at least one glitazone compound. In other words, no active pharmaceutical ingredient other than the at least one glitazone compound may be applied to the affected area of the skin of the individual.

In an embodiment of the invention, is a pharmaceutical formulation for topical application to the skin of an individual comprising at least one glitazone compound and a pharmaceutically acceptable vehicle or carrier in which the at least one glitazone compound is dissolved, suspended, dispersed, or emulsified.

In the foregoing embodiment of the invention, the at least one glitazone compound may be selected from the group consisting of pioglitazone, rosiglitazone, lobeglitazone, troglitazone, netoglitazone, rivoglitazone, and ciglitazone.

In each of the foregoing embodiments: a) when the at least one glitazone compound is pioglitazone, then the formulation may be free of petrolatum; or b) the formulation may comprise at least one glitazone compound, petrolatum, and one or more additional ingredients.

In each of the foregoing embodiments, the pharmaceutical formulation may be in the form selected from the group consisting of creams, lotions, ointments, solutions, emulsions, gels, sprays, and foams.

In each of the foregoing embodiments, the pharmaceutical formulation may not contain any active pharmaceutical ingredient other than the at least one glitazone compound.

In an embodiment of the invention is a method of increasing lipid content in sebocytes in an individual, the method comprising contacting sebocytes with at least one glitazone compound in an amount sufficient to increase the lipid content of the sebocytes, wherein the at least one glitazone compound travels from an outer surface of the skin of the individual to an inner portion of the skin. In the foregoing embodiment, the individual may be male or female and the treated area of the skin may not include the vulvar region of the female.

In each of the foregoing embodiments, the at least one glitazone compound is selected from the group consisting of pioglitazone, rosiglitazone, lobeglitazone, troglitazone, netoglitazone, rivoglitazone, and ciglitazone.

In each of the foregoing embodiments, the at least one glitazone compound may be in the form of a pharmaceutically acceptable salt, hydrate, solvate, or prodrug.

In each of the foregoing embodiments, the method consists essentially of contacting sebocytes with at least one glitazone compound in an amount sufficient to increase the lipid content of the sebocytes, wherein the at least one glitazone compound travels from an outer surface of the skin of the individual to an inner portion of the skin.

DETAILED DESCRIPTION

Detailed illustrative embodiments of the present invention are disclosed herein. However, specific structural and functional details disclosed herein are merely representative for purposes of describing example embodiments of the present invention. The present invention may be embodied in many alternate forms and should not be construed as limited to only the embodiments set forth herein. Further, the terminology used herein is for the purpose of describing particular embodiments only and is not intended to be limiting of example embodiments of the invention.

As used herein, the singular forms "a," "an," and "the," are intended to include the plural forms as well, unless the context clearly indicates otherwise. It further will be understood that the terms "comprises," "comprising," "includes," and/or "including," specify the presence of stated features, steps, or components, but do not preclude the presence or addition of one or more other features, steps, or components. The transitional phrase "consisting essentially of" or "consists essentially of" limits the scope of a claim to the specified materials or steps and those that do not materially affect the basic and novel characteristics of the claimed invention. Herein, the basic and novel characteristics of the claimed invention is the property of ameliorating the signs and symptoms in subjects suffering from a dermatologic condition associated with a decrease in number or function of sebocytes.

As used herein, the term "effective amount" of an agent, such as a pharmaceutical formulation, refers to an amount effective, at dosages and for periods of time necessary, to achieve the desired therapeutic or prophylactic result.

The term "individual" or "subject" as used herein refers to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "pharmaceutical formulation" as used herein refers to a preparation which is in such form as to permit the biological activity of an active ingredient contained therein to be effective, and which contains no additional components which are unacceptably toxic to a subject to which the formulation would be administered.

The term "treatment," "treat," or "treating" as used herein refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, pharmaceutical formulations of the invention are used to delay development of a disease or to slow the progression of a disease, or reduce the severity of a disease.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, a disclosure of specific amounts/values of a component, compound, substituent, or parameter in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

It has been unexpectedly discovered that topical treatment with a pharmaceutical formulation containing at least one glitazone is effective in ameliorating the signs and symptoms in subjects suffering from a dermatologic condition associated with a decrease in number or function of sebocytes, such as keratosis pilaris (KP). This discovery was especially surprising in view of the fact that retinoids, compounds that reduce the secretion of sebum, are often effective in treating KP. This discovery is even more surprising in view of the fact that KP appears to be due to a plugging of follicles, so that increasing the amount of sebum within a blocked follicle would not be expected to have an advantageous effect. Glitazones, in contrast to retinoids, increase the secretion of sebum from sebocytes.

Although not wishing to be bound by theory, it is conceived that, not only do glitazone compounds increase the secretion of sebum from sebocytes, but glitazone compounds also stimulate the development of additional sebocytes in skin that contains an abnormally low number of sebocytes. It is also conceived that, in patients with KP, sebocytes make lipids that lead to plugging and that glitazones may function to change the lipid profile in the follicle, thereby ameliorating the keratotic plug.

The at least one glitazone compound that may be used in accordance with the method of this application include, but are not limited to, pioglitazone, rosiglitazone, lobeglitazone, troglitazone, netoglitazone, rivoglitazone, and ciglitazone. Two or more glitazone compounds, or three or more glitazone compounds may be used in accordance with the method of this application. Various forms of glitazone compounds may be utilized including, but not limited to, the free base, or a salt. For instance, the glitazone compound may be in the form of a salt, and examples of such a salt include a pharmaceutically acceptable salt such as salts with inorganic bases, salts with organic bases, salts with inorganic acids, salts with organic acids, salts with basic or acidic amino acids, and the like. Preferable examples of the salts with inorganic bases include salts with alkali metals such as sodium, potassium, etc.; alkaline earth metals such as calcium, magnesium, etc.; aluminum; ammonium; and the like. Preferable examples of the salts with organic bases include salts with trimethylamine, triethylamine, pyridine, picoline, ethanolamine, diethanolamine, triethanolamine, dicyclohexylamine, N,N-dibenzylethylenediamine, etc. Preferable examples of the salts with inorganic acids include salts with hydrochloric acid, hydrobromic acid, nitric acid, sulfuric acid, phosphoric acid, etc. Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc. Preferable examples of the salts with basic amino acids include salts with arginine, lysine, ornithine, etc., and preferable examples of the salts with acidic amino acids include salts with aspartic acid, glutamic acid, etc. In addition, the glitazone compound may be any of anhydrides and hydrates. The glitazone compound is preferably pioglitazone or a salt thereof (preferably hydrochloride), or rosiglitazone or a salt thereof (preferably maleate), more preferably pioglitazone or a salt thereof, and even more preferably pioglitazone hydrochloride. The glitazone compound may also be present as a complex or as a prodrug.

Dermatologic conditions that are associated with a decrease in number of sebocytes and that may be treated in accordance with the method of this application include but are not limited to keratosis pilaris, acanthosis nigricans, atopic dermatitis, ulerythema oophorygenes, xerosis, and icythyosis.

Thus, in one embodiment, the invention is a method for increasing sebum production in an individual suffering from a dermatologic condition associated with a decrease in sebum production. According to this embodiment, a pharmaceutical formulation containing an amount of at least one glitazone compound effective to increase the production of sebum is applied to areas of the body affected by the dermatologic condition.

In each of the foregoing embodiments, the dermatologic condition may be one in which the affected area contains fewer sebocytes than are present in skin of an individual who is not affected by the dermatologic condition. For purposes of this application, this comparison of number of sebocytes pertains to equivalent areas of the body. That is, for example and to illustrate this point, skin of the scalp in an affected individual is compared to skin of the scalp in a non-affected individual, skin of the trunk in an affected individual is compared to skin of the trunk in a non-infected individual, skin of the face in an affected individual is compared to skin of the face in a non-infected individual, and skin of the buttocks in an affected individual is compared to skin of the buttocks in a non-infected individual.

In each of the foregoing embodiments, the at least one glitazone compound may be applied to the affected areas in a formulation for topical administration. Such formulations may be in any form suitable for topical application to the skin, such as creams, lotions, ointments, solutions, emulsions, gels, sprays, and foams.

In each of the foregoing embodiments, the formulation containing the at least one glitazone compound may further contain a pharmaceutically acceptable vehicle or carrier in which the at least one glitazone compound is dissolved, suspended, emulsified, or otherwise dispersed. Examples of suitable vehicles or carriers may be individual ingredients or mixtures thereof including water, ethanol, polyols such as propylene glycol, polyethylene glycol, and glycerol, vegetable oils, mineral oil, petrolatum, and organic esters. In each of the foregoing embodiments, the formulation containing the at least one glitazone compound may be free of petrolatum and preferably may be free of ingredients containing a hydrocarbon, or contains ingredients, such as excipients, other than the at least one glitazone and petrolatum or hydrocarbon-containing ingredient.

In each of the foregoing embodiments, the formulations may comprise a glitazone compound, ethoxy diglycol (TRANSCUTOL® P (Gattefosse, Lyon, France), propylene glycol, benzyl alcohol, laureth-4, and 95% ethanol.

In accordance with the method of the invention, a pharmaceutical formulation containing at least one glitazone compound is administered to skin of an individual affected by a dermatologic condition that is associated with a decrease in number or function of sebocytes. The pharmaceutical formulation may be administered at a frequency and for a duration sufficient to ameliorate the signs and/or symptoms of the dermatologic condition. The frequency of application to the affected skin area may vary from one to four times daily. After the condition is under control, the glitazone compound formulation may be applied less frequently if desired, such as one or more times every other day or weekly. Treatment duration may range from 2 weeks to indefinitely. In each of the foregoing embodiments, the treatment duration may be for about 12 weeks and may be repeated as necessary to control the signs and symptoms of the skin condition. In each of the foregoing embodiments, the at least one glitazone compound may not be applied to the vulva region.

Preferably, the at least one glitazone compound is pioglitazone, although other glitazone compounds may be used in addition to, or in place of, pioglitazone. Other suitable glitazone compounds include rosiglitazone, lobeglitazone, troglitazone, netoglitazone, rivoglitazone, and ciglitazone. The at least one glitazone compound may be used without any other active pharmaceutical ingredient or may be used in combination with at least one active pharmaceutical ingredient selected from the group consisting of (i.e., limited to) a corticosteroid, a retinoid, and an exfoliant, which other agent may be contained within the same formulation as the at least one glitazone compound or may be applied in a separate formulation. Herein, the term "active pharmaceutical ingredient" is defined as any substance or combination of substances used in a finished pharmaceutical product, intended to furnish pharmacological activity or to otherwise have direct effect in the diagnosis, cure, mitigation, treatment or prevention of disease, or to have direct effect in restoring, correcting or modifying physiological functions in human beings. For instance, active pharmaceutical ingredients that may be excluded from the inventive formulation include one or more agents that therapeutically affect the androgen receptor signaling pathway (other than the glitazone compounds described herein) such as an antiandrogen agent; antibiotic agents; anti-inflammatory agents; and autotaxin inhibitor agents. For instance, an active pharmaceutical ingredient would not be a vehicle, carrier, or excipient, such as those described herein. The corticosteroids that may be used include but are not limited to one or more of hydrocortisone, hydrocortisone valerate, hydrocortisone butyrate, desonide, fluocinolone acetonide, halobetasol propionate, clobetasol propionate, triamcinolone acetonide, betamethasone valerate, betamethasone dipropionate, halcinonide, diflorasone diacetate, desoximetasone, prednicarbonate, clocortolone pivalate, fluticasone propionate, and flurandrenolide. The retinoids that may be used, include but are not limited to one or more of tretinoin, tazarotene, isotretinoin, adapalene, bexarotene, acitretin, etretinate, alitretinoin, and retinol. The exfoliant that may be used, include but are not limited to one or more of an alpha-hydroxy acid and beta-hydroxy acid, such as glycolic acid, lactic acid, malic acid, citric acid, alpha-hydroxyoctanoic acid, alpha-hydroxycaprylic acid, and hydroxycaprylic acid and salicylic acid.

In certain embodiments of the invention is a method of treating KP in which pioglitazone is used in a topical formulation to enhance the effectiveness of exfoliants, such as beta hydroxy acids or alpha hydroxy acids, such as lactic acid, retinoids, and/or corticosteroids by combining one or more exfoliant, retinoid, and corticosteroids in the same formulation with the pioglitazone, preferably in a cream, and applying the cream to the affected skin of a person with KP.

The concentration of the at least one glitazone compound that is contained within the formulation is that which is effective to ameliorate the signs and/or symptoms of the dermatologic condition. The optimal concentration of the at least one glitazone compound may be varied depending on several factors, including the particular glitazone compound present in the formulation. Generally, the concentration will range between 0.01 to 10% w/w, although concentrations higher or lower than this range may be used if desired. Specific examples of suitable concentrations of the at least one glitazone compound in the formulation may be 0.05, 0.075, 0.1, 0.2, 0.25, 0.5, 1.0, 2.0, 2.5, 5, 7.5, and 10% w/w.

Among the pharmaceutically suitable glitazones, pioglitazone is the most preferred glitazone. Pioglitazone can be used as the hydrochloride or the free base, which can be solubilized, partially solubilized, emulsified or suspended.

Micronized pioglitazone HCl is the preferred form when the active drug substance is in suspended or partially solubilized form.

Of the suitable dosage topical forms for pioglitazone, emulsions, gels and ointments are preferred. Emulsions are the most preferred (i.e., creams and lotions). Emulsions can be water-in-oil, oil-in-water or micro-emulsions.

The ingredients used in topical formulations are pharmaceutically suitable in all respects including safety for use on the skin, purity, freedom from contaminants and the like. The ingredients, sometimes called excipients, may be classified various ways including by function. However, many excipients can have more than one function in a topical formulation. The types of excipients that may be used in creams and lotions of this invention are described as follows.

Emulsions are inherently thermodynamically unstable and must be stabilized by the addition of an emulsifier (emulsifying agent). Emulsions include lotions, which are comparatively low viscosity and pourable, and creams which are more viscous and cannot be poured. There are two basic types of emulsions: oil in water (O/W) and water in oil (W/O). Emulsions are not limited to the basic types. Other emulsion types include but are not limited to multi-phase emulsions with more than 2 phases, such as oil in water in oil emulsion, and microemulsions. Emulsifiers are a group of chemicals belonging to the surfactant family. Surfactants are any ingredients that lower tension between a surface and a liquid or between two immiscible liquids. Examples of emulsifiers include: ceteth 20, sodium laureth sulfate, cetomacrogol 1000, cholesterol, steareth 2, steareth 21, sodium lauryl sulfate, and PEG 100 stearate.

Delivery aids are a group of substances that enhance or improve the delivery of pioglitazone into the skin when used alone or in combination in a topical pioglitazone formulation. Delivery Aids for pioglitazone according to this invention are one or more ingredients selected from the group of ethoxydiglycol, propylene glycol, isostearic acid, DMSO, laureth 4 and C12-15 Alkyl Benzoates.

Emollients are water insoluble oils, lipids and fats that coat and lubricate the skin and make it smooth and supple. Examples of emollients used in creams and lotions are: synthetic esters, such as isopropyl palmitate, isopropyl myristate, diisopropyl adipate and diethyl sebecate; hydrocarbons, such as light mineral oil, mineral oil and white petrolatum; natural vegetable oils, such as peanut oil; and lanolin and its components, such as lanolin oil.

Lipophilic Thickeners include pharmaceutical grade fatty acids, such as stearic acid; fatty alcohols, such as cetyl alcohol, stearyl alcohol, cetostearly alcohol; waxes such as white wax, paraffin and microcrystalline wax.

Polymeric Thickeners include carbomers, such as, carbomer 934P, 940, 980, and 941. Other cellulosic and other pharmaceutically acceptable water-soluble polymers are useful as polymeric thickeners for emulsions including, carboxymethyl cellulose, methylcellulose, hydroxyethyl cellulose, and hydroxymethyl cellulose, and xanthan gum. Also high molecular weight polyethylene glycols, such as PEG 4000, may be used as polymeric thickeners.

Another excipient that can be used in the inventive topical formulation is a pH adjuster. These pH Adjusters are used to attain a particular pH or pH range of the cream or lotion. Examples of pH adjusters comprise acids, bases and buffers, such as, tromethamine, trolamine, ethanolamine, sodium hydroxide, hydrochloric acid, acetic acid, citric acid, citrate buffer, and phosphate buffer. When the term "about" is used with respect to a pH adjustment of an emulsion, it is intended to be +/−0.5, i.e., "about pH 8" means pH of 7.5 to 8.5.

Antimicrobial Preservatives are pharmaceutically and topically safe ingredients that inhibit growth of bacteria and fungi which might be present as minor contaminants in the ingredients of the emulsion, might be introduced during manufacturing and packaging, or be introduced during usage of the product by the patient being treated with the cream or lotion. Topical emulsions are not made to be sterile; therefore, antimicrobial preservatives are necessary to prevent spoilage during the product's shelf life. Examples of antimicrobial preservatives include benzyl alcohol, methyl paraben, propyl paraben, and imidurea.

Other Excipients cover a diverse group of possible ingredients, such as, anti-oxidants, colorants, fragrances, solvents, humectants (e.g., glycerin, polyethylene glycol 400), API stabilizers, wetting agents, suspending agents, and stabilizers.

Purified Water is the universal ingredient of pharmaceutical emulsions. It comprises a large part of the external phase of oil-in-water emulsions, and it is almost always part of the internal phase of water-in-oil emulsions. Because of its wide central role in emulsion formulations, it is sometimes referred to as a carrier. Purified water is the pharmaceutically preferred type of water for topical pharmaceutical dosage forms.

| General Composition for a pioglitazone emulsion (cream or lotion) | | | |
|---|---|---|---|
| Ingredient Type | Concentrations (By Weight) | Preferred Concentrations | Most Preferred Concentrations |
| Pioglitazone (active ingredient) | 0.05 to 5 | 0.1 to 2.5 | 0.5 to 1.5 |
| Delivery Aids for pioglitazone | 5 to 80 | 10 to 70 | 15 to 65 |
| Emulsifier(s) | 0.25 to 15 | 1 to 10 | 1.5 to 8 |
| Emollient(s) | 0.25 to 85 | 1 to 50 | 2.5 to 40 |
| Lipophilic Thickener(s) | 0 to 25 | 0.5 to 20 | 1 to 15 |
| Polymeric Thickener(s) | 0 to 2.5 | 0.1 to 1.75 | 0.25 to 1.25 |
| pH Adjuster(s) | q.s. | q.s. | q.s. |
| Antimicrobial Preservative(s) | q.s. | q.s. | q.s. |
| Other Excipient(s) | q.s. | q.s. | q.s. |
| Purified Water | q.s. ad 100 | q.s. ad 100 | q.s. ad 100 |

Pioglitazone emulsions are illustrated in prophetic Examples A through E.

| INGREDIENT | PERCENT BY WEIGHT |
|---|---|
| Example A - Pioglitazone Lotion | |
| Pioglitazone HCL, micronized | 0.75 |
| Cetostearyl alcohol | 5.25 |
| Ceteth 20 | 2.00 |
| Imidurea | 0.20 |
| Methyl Paraben | 0.20 |
| Propyl Paraben | 0.10 |
| Isopropyl Myristate | 2.50 |
| Propylene Glycol | 20.00 |
| Purified Water q.s. ad | 100.00 |
| Example B - Pioglitazone Cream | |
| Pioglitazone HCL | 0.75 |
| Cetostearyl alcohol | 5.25 |
| White Petrolatum | 5.00 |
| White Wax | 3.50 |
| Cetomacrogol 1000 | 1.00 |
| Laureth 4 | 4.00 |
| Benzyl Alcohol | 2.50 |
| Propylene Glycol | 10.00 |

| INGREDIENT | PERCENT BY WEIGHT |
|---|---|
| Ethoxydiglycol | 10.00 |
| Purified Water q.s. ad | 100.00 |
| Example C - Pioglitazone Cream | |
| Pioglitazone HCL | 0.50 |
| Stearyl Alcohol | 3.25 |
| White Wax | 4.00 |
| Ceteth 20 | 0.75 |
| Laureth 4 | 4.00 |
| Benzyl Alcohol | 1.50 |
| DMSO | 30.00 |
| Isopropyl Myristate | 6.00 |
| Carbomer 940 | 0.25 |
| Trolamine q.s. ad | pH 5.5-6.5 |
| Purified Water q.s. ad | 100.00 |
| Example D - Pioglitazone Lotion | |
| Pioglitazone HCL | 1.00 |
| Laureth 4 | 3.50 |
| Sodium Laureth Sulfate | 3.50 |
| Benzyl Alcohol | 1.50 |
| Propylene Glycol | 7.50 |
| DMSO | 50.00 |
| Isopropyl Myristate | 3.50 |
| Light Mineral oil | 2.00 |
| Cetyl Alcohol | 1.50 |
| Carbomer 941 | 0.50 |
| Tromethamine q.s. ad | pH 5-6.5 |
| Purified Water q.s. ad | 100.00 |
| Example E - Pioglitazone Cream | |
| Pioglitazone HCL | 1.00 |
| Cetostearyl alcohol | 5.25 |
| Ceteth 20 | 1.25 |
| Laureth 4 | 4.00 |
| Benzyl Alcohol | 2.50 |
| Propylene Glycol | 2.00 |
| C12-15 Alkyl Benzoates | 10.00 |
| Diisorpopyl Adipate | 7.50 |
| Isopropyl Myristate | 7.50 |
| Diethyl Sebecate | 10.00 |
| Carbomer 940 | 0.25 |
| Trolamine q.s. ad | pH ca. 8.0 |
| Purified Water q.s. ad | 100.00 |

The following Examples F-I provide prophetic formulations of pioglitazone ointments and gels.

| INGREDIENT | PERCENT BY WEIGHT |
|---|---|
| Example F - Pioglitazone Ointment | |
| Pioglitazone HCl, micronized | 1.00 |
| Ethoxydiglycol | 5.00 |
| Isostearic Acid | 3.00 |
| C12-15 Alkyl Benzoates | 7.50 |
| Cholesterol | 3.50 |
| Laureth 4 | 1.50 |
| White Wax | 8.00 |
| Stearyl Alcohol | 5.00 |
| White Petrolatum q.s. ad | 100.00 |
| Example G - Pioglitazone Ointment | |
| Pioglitazone HCl, micronized | 1.50 |
| Propylene Glycol | 10.00 |
| Benzyl Alcohol | 1.50 |
| Cholesterol | 3.50 |
| Laureth 4 | 1.50 |
| White Wax | 8.00 |
| Stearyl Alcohol | 3.00 |
| White Petrolatum q.s. ad | 100.00 |
| Example H - Pioglitazone Gel | |
| Pioglitazone HCL | 1.00 |
| Laureth 4 | 4.00 |

| INGREDIENT | PERCENT BY WEIGHT |
|---|---|
| Benzyl Alcohol | 1.50 |
| Propylene Glycol | 7.50 |
| DMSO | 50.00 |
| Ethyl Alcohol | 5.00 |
| Isopropyl Myristate | 2.00 |
| Carbomer 940 | 0.75 |
| Trolamine q.s. ad | pH about 6 |
| Purified Water q.s. ad | 100.00 |
| Example I - Pioglitazone Gel | |
| Pioglitazone HCL | 1.00 |
| Laureth 4 | 4.00 |
| Benzyl Alcohol | 1.50 |
| Propylene Glycol | 7.50 |
| DMSO | 30.00 |
| Isopropyl Myristate | 3.50 |
| Hydroxypropyl Cellulose | 0.75 |
| Ethyl Alcohol q.s. ad | 100.00 |

The invention is further illustrated in the following non-limiting examples.

Example 1—Preparation of Pioglitazone Formulation for Topical Application

Thirty tablets of 15 mg (450 mg total) pioglitazone ([(±)-5-[[4-[2-(5-ethyl-2-pyridinyl) ethoxy] phenyl] methyl]-2,4-] thiazolidinedione monohydrochloride) (ACTOS™, Takeda Pharmaceuticals America, Inc., Deerfield, Ill.) were crushed by mortar and pestle until a uniform fine powder was obtained and the powder was then transferred to a wide mouth jar. This powder was combined with fifty (50) ml of a vehicle containing ethoxy diglycol (TRANSCUTOL® P (Gattefosse, Lyon, France) 20%, propylene glycol 20%, benzyl alcohol 5%, laureth-4 4%, and 95% ethanol 51% by weight to obtain a 1% formulation w/w of pioglitazone. The jar was sealed in order to prevent evaporation of the alcohol in the mixture. The mixture was then stirred by use of a magnetic stirrer for 24 hours. The formulation was then transferred to a 2 ounce polyethylene bottle with a Dab-O-Matic® applicator and cap (Dab-O-Matic Corporation, 896 S. Columbus Ave., Mt. Vernon, N.Y.). Prior to use, the mixture was well shaken.

Example 2—Treatment of Keratosis Pillaris

A 19-year-old female patient with Fitzpatrick skin type 3 who had KP since childhood on her arms had previously used moisturizers, but reported that these treatments were not effective. The affected areas of her arms were treated with the 1% pioglitazone of Example 1 twice per day for 12 weeks. Prior to treatment, the severity of the KP condition was graded. At baseline before treatment, erythema was graded as severe, follicular papules were graded as severe, and the amount of xerosis was graded as moderate. After 12 weeks of treatment, the erythema was graded as mild, the follicular papules were graded as moderate, and the amount of xerosis was graded as none. Following treatment, the patient stated that she had a favorable view of the treatment and that she had experienced no irritation due to the treatment.

Example 3—Treatment of Keratosis Pillaris

A 29-year-old female patient with Fitzpatrick skin type 2 who had KP since childhood on her arms and legs had previously used moisturizers, but reported that these treatments were not effective. The affected areas of her arms were treated with the 1% pioglitazone of Example 1 twice per day for 12 weeks. Prior to treatment, the severity of the KP condition was graded. At baseline before treatment, erythema was graded as severe, follicular papules were graded as moderate, and the amount of xerosis was graded as mild. After 12 weeks of treatment, the erythema was graded as mild, the follicular papules were graded as mild, and the amount of xerosis was graded as mild. Following treatment, the patient stated that she had a favorable view of the treatment and that she had experienced no irritation due to the treatment.

Example 4—In Vitro Treatment of Cultured Sebocytes

Cultured SEB-1 sebocytes (Xia et al., Dermato-Endocrinology, 1(2):92-95 (2009)) were treated with the pioglitazone formulation of Example 1. Sebocytes were cultured in 96 wells plates (2500 cells/well), until confluency. Plates were washed twice with warm sterile PBS and then incubated (at 37° C. and 5% $CO_2$) for another 48 hours after treating them with the pioglitazone formulation in treatment media. After 48 hours, media was carefully removed from the plates and, after washing with PBS, ADIPORED™ reagent (Lonza Walkersville, Inc., Walkersville, Md.) was carefully added into each well. The plates were read for intracellular lipids using a spectrofluorometer. The lipid fluorescence was normalized against the total cell count that was performed using DAPI staining. Following treatment, the lipid content in the treated sebocytes was determined to have increased by 27% compared to control untreated sebocytes. The increased lipid content was confirmed by determining the expression of SREBP-1, a lipid synthesis transcription factor.

Example 5—Rosiglitazone

A formulation for topical application similar to that of Example 1 that contains rosiglitazone instead of pioglitazone is made. Examples 2 to 4 are repeated, except that the formulation containing rosiglitazone is substituted for that containing pioglitazone. Results similar to those obtained in Examples 2 to 4 using pioglitazone are obtained using rosiglitazone.

Example 6—Lobeglitazone

A formulation for topical application similar to that of Example 1 that contains lobeglitazone instead of pioglitazone is made. Examples 2 to 4 are repeated, except that the formulation containing lobeglitazone is substituted for that containing pioglitazone. Results similar to those obtained in Examples 2 to 4 using pioglitazone are obtained using lobeglitazone.

Example 7—Troglitazone

A formulation for topical application similar to that of Example 1 that contains troglitazone instead of pioglitazone is made. Examples 2 to 4 are repeated, except that the formulation containing troglitazone is substituted for that containing pioglitazone. Results similar to those obtained in Examples 2 to 4 using pioglitazone are obtained using troglitazone.

Example 8—Netoglitazone

A formulation for topical application similar to that of Example 1 that contains netoglitazone instead of pioglitazone is made. Examples 2 to 4 are repeated, except that the formulation containing netoglitazone is substituted for that containing pioglitazone. Results similar to those obtained in Examples 2 to 4 using pioglitazone are obtained using netoglitazone.

Example 9—Rivoglitazone

A formulation for topical application similar to that of Example 1 that contains rivoglitazone instead of pioglitazone is made. Examples 2 to 4 are repeated, except that the formulation containing rivoglitazone is substituted for that containing pioglitazone. Results similar to those obtained in Examples 2 to 4 using pioglitazone are obtained using rivoglitazone.

Example 10—Ciglitazone

A formulation for topical application similar to that of Example 1 that contains ciglitazone instead of pioglitazone is made. Examples 2 to 4 are repeated, except that the formulation containing ciglitazone is substituted for that containing pioglitazone. Results similar to those obtained in Examples 2 to 4 using pioglitazone are obtained using ciglitazone.

Further modifications, uses, and applications of the invention described herein will be apparent to those skilled in the art. It is intended that such modifications be encompassed in the following claims.

All documents mentioned herein are hereby incorporated by reference in their entirety or alternatively to provide the disclosure for which they were specifically relied upon. Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments.

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

What is claimed is:

1. A method for treating a dermatologic condition that is associated with a decrease in number or function of sebocytes, the method comprising topically applying to skin of an individual affected by the dermatologic condition a pharmaceutical formulation comprising a therapeutically effective amount of at least one glitazone compound, wherein the dermatologic condition is keratosis pilaris.

2. The method of claim 1, wherein the pharmaceutical formulation comprises a vehicle or carrier in which the at least one glitazone compound is dissolved, dispersed, suspended, or emulsified.

3. The method of claim 1, wherein the at least one glitazone compound is selected from the group consisting of pioglitazone, rosiglitazone, lobeglitazone, troglitazone, netoglitazone, rivoglitazone, and ciglitazone.

4. The method of claim 3, wherein the at least one glitazone compound is pioglitazone.

5. The method of claim 1, wherein the pharmaceutical formulation is in the form selected from the group consisting of creams, lotions, ointments, solutions, emulsions, gels, sprays, and foams.

6. The method of claim 1, further comprising applying to the skin at least one other active pharmaceutical ingredient selected from the group consisting of a corticosteroid, a retinoid, and an exfoliant, wherein the at least one other active pharmaceutical ingredient is contained within the same pharmaceutical formulation as the at least one glitazone compound or is applied in a separate pharmaceutical formulation.

7. The method of claim 1, wherein the pharmaceutical formulation does not contain any active pharmaceutical ingredient other than the at least one glitazone compound.

8. The method of claim 1, wherein the at least one glitazone compound is in the form of a pharmaceutically acceptable salt, hydrate, solvate, or prodrug.

9. The method of claim 1, wherein the concentration of the glitazone compound is between about 0.01 to 10% w/w.

* * * * *